United States Patent [19]

Spencer

[11] Patent Number: 5,024,217
[45] Date of Patent: Jun. 18, 1991

[54] BANDAGE APPLICATOR

[75] Inventor: Dennis S. Spencer, Ingle Farm, Australia

[73] Assignee: Olemunda Pty. Ltd., Kilkenny, Australia

[21] Appl. No.: 404,419

[22] Filed: Sep. 7, 1989

Foreign Application Priority Data

Sep. 14, 1988 [AU] Australia ............................. PJ0422

[51] Int. Cl.⁵ .................... A61F 13/00; A61F 15/00
[52] U.S. Cl. ..................................... 128/82; 128/156; 128/849; 156/277
[58] Field of Search ................. 128/82, 156, 849, 851; 156/277, 303.1, 583.7, 583.1

[56] References Cited

U.S. PATENT DOCUMENTS 3,597,293 8/1971 Willett .................................. 156/277
3,674,622 7/1972 Plasse .................................. 156/277
4,545,371 10/1985 Grossmann et al. ................. 128/156

OTHER PUBLICATIONS

Australian DR, "Glove Handy for Burns", Feb. 6, 1987.

Primary Examiner—Randall L. Green
Assistant Examiner—Paul Prebilic
Attorney, Agent, or Firm—Edward W. Callan

[57] ABSTRACT

An applicator for applying adhesive plastics film to the hands or other extremities of the human has two foam-filled moulded trays hinged together at one end and releasably latched at the other end, which itself has a part-recess in each of the trays which allow access to the space between the trays, one at least of the trays having film retaining means extending along it.

5 Claims, 3 Drawing Sheets

BANDAGE APPLICATOR

This invention relates to applicator and to hinge which is useful with such an applicator, (although the hinge is useful for other purposes).

BACKGROUND OF THE INVENTION

It is now recognised medically that it is desirable to cover a wound (cut, burn, or the like) with a thin film of permeable plastics material to protect the surrounding area against infection and to provide means whereby healing can commence readily.

Most such wounds occur with the hands, and heretofore it has been common practice to merely bandage a hand but this requires considerable time. One object of this invention is to provide an applicator which is suitable for quickly applying an adhesive permeable film over a wound, and particularly over a wound on a hand, a foot, or other extremity of the body.

Different manufacturers produce suitable films for use in applicators, and for example one such film is sold by the English company Smith and Nephew under the Trade Mark "OpSite", but there are other companies in other countries which supply similar film. The film is characterised by having one side with an adhesive substance on a thin plastics film, and having a "peel-off paper" which normally covers the film.

BRIEF SUMMARY OF THE INVENTION

In this invention, an applicator for applying adhesive plastics film to the hands or other extremities of the human has two foam-filled moulded trays hinged together at one end and releasably latched at the other end, which itself has a part-recess in each of the trays which allow access to the space between the trays, one at least of the trays having film retaining means extending along it.

More specific one aspect the invention consists of a pair of moulded trays, respective soft resilient foam pads in said tray, a hinge joining corresponding first ends of the trays such that the foam pads are openable away from each other or closable to lie in face-to-face contiguity, latch means releasably joining second ends of the trays which are opposite the first ends when the foam pads are in their face-to-face contiguity, each second end having a part recess co-operable with the other part recess to form an access opening at the second end, and film retaining means extending along opposite sides of at least one of the trays.

No prior art is known by the Applicant nor by the Inventor which preceded the Inventor's development of this invention. Thus with this invention a person with, say, a burn, scald or cut in his hand, can have that hand dressed by merely securing two sheets of film, one to each of the trays, placing the hand over one sheet and closing the other tray, thereby firmly pressing the adhesive surfaces of the film into contact with the skin, and subsequently trimming the peripheral material which is not required.

BRIEF DESCRIPTION OF THE DRAWINGS

An embodiment of the invention is described hereunder in some detail with reference to and is illustrated in the accompanying drawings in which.

DESCRIPTION OF THE PREFERRED EMBODIMENTS

Figure 1:
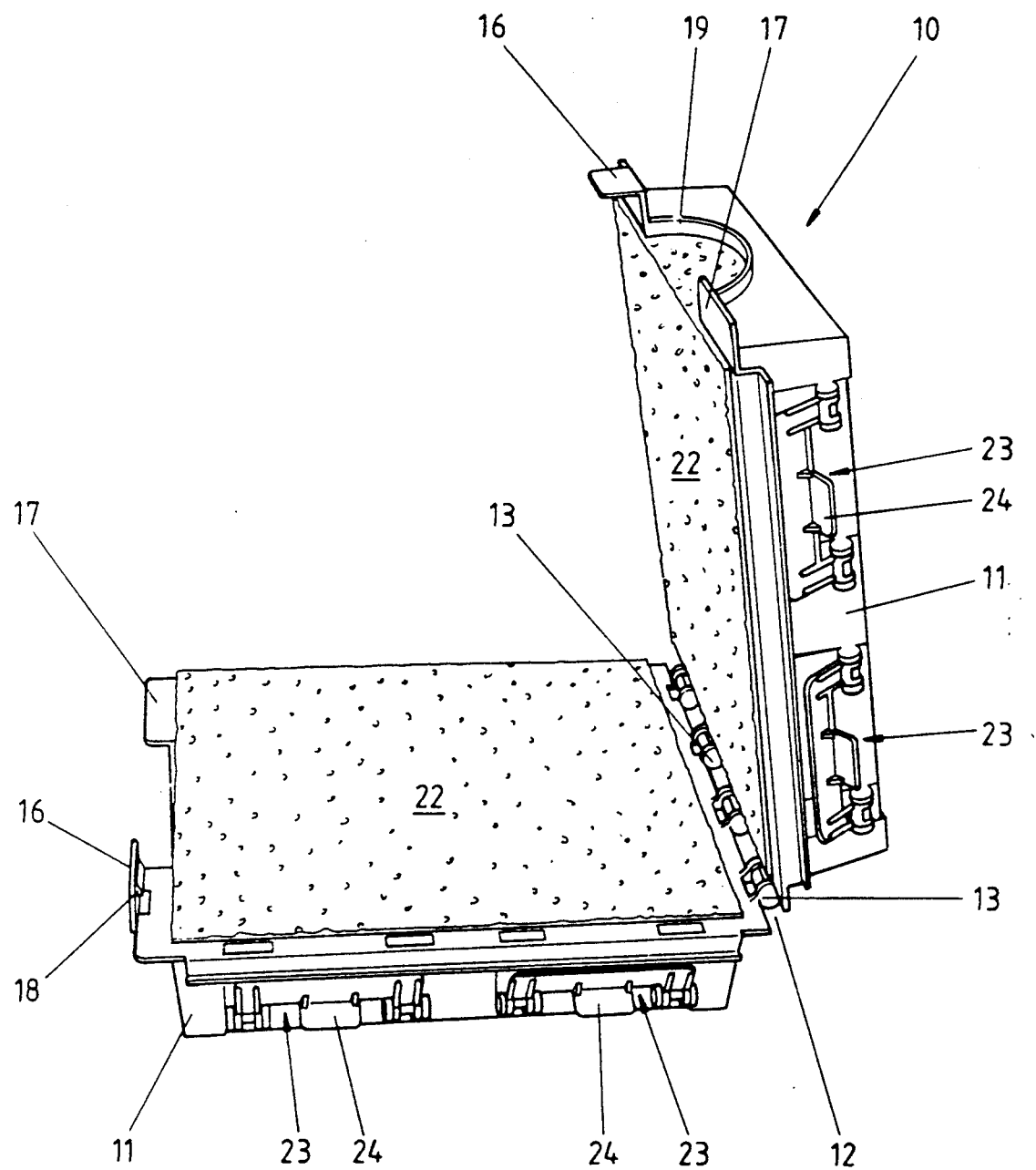
FIG. 1 is a perspective view of an applicator.

In this embodiment, an applicator 10 comprises two moulded trays 11 which are identical, or nearly identical. Each moulded tray 11 is provided with hinge portions 12 (see FIG. 4) one hinge portion 12 having a bar 13 and the other hinge portion having a part-circular hook-like claw 14 which is positionable over a bar 13 and engages part way around the bar when one tray is positioned over an identical tray. Upon inverting one tray with respect to the other, the bar and claw "changes sides", and these members remain co-operable.

Figure 3:
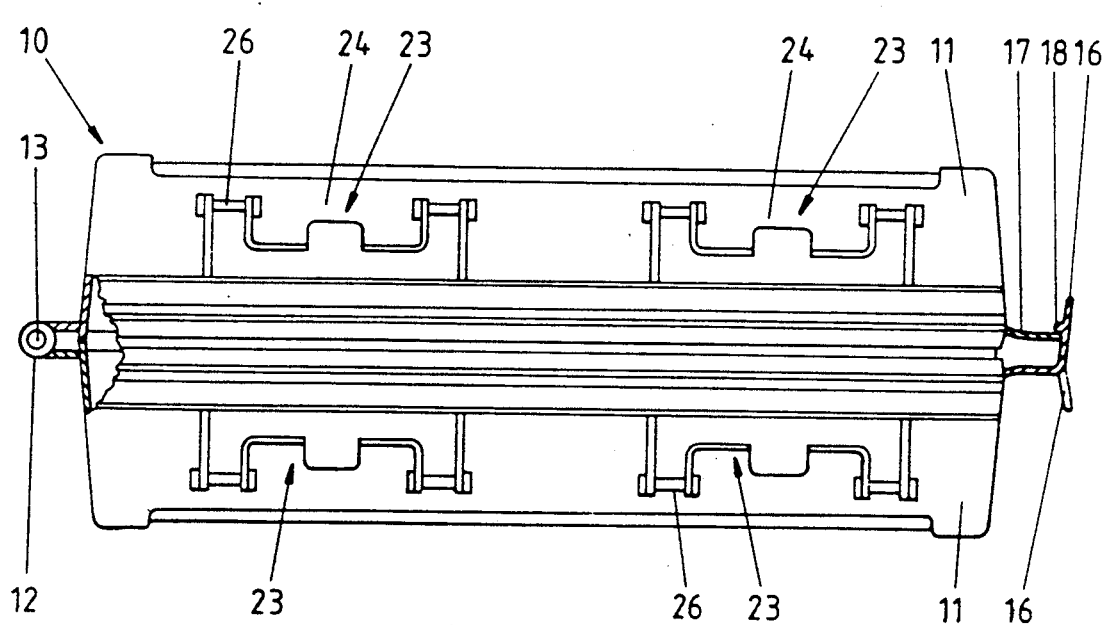
FIG. 3 is a side elevation of FIG. 2 drawn partly in section.

Along the sides opposite the hinge portions, there are provided a pair of interengaging clips 16 which engage as best seen in FIG. 3. The clips are identical but one clip faces upwardly and the other faces downwardly, and the interengagement is flange 17 which projects from the side of the tray, each clip 16 having a projection 18 which snaps over the flange 17.

Figure 4:
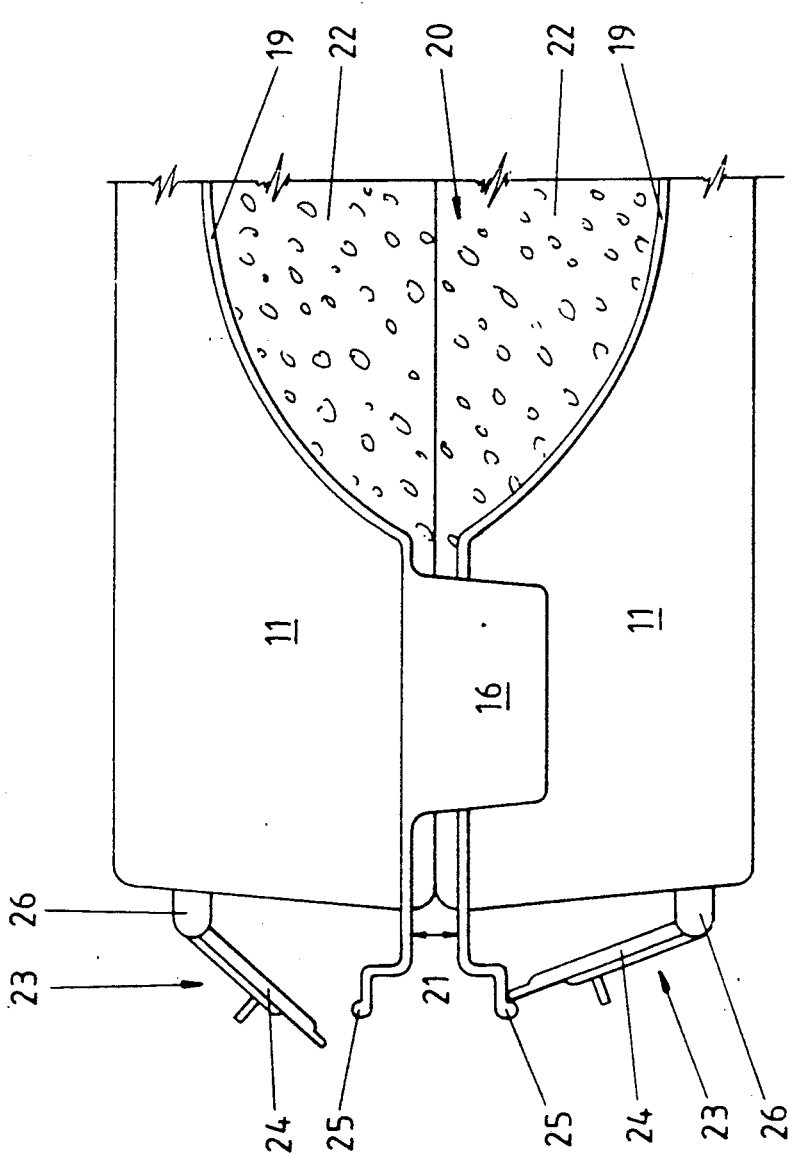
FIG. 4 is a part end elevation of FIG. 1 but drawn to a larger scale.

As seen best in FIG. 4, the end walls of the trays 11 are provided with recess flanges 19 which, when the trays are closed together, provide an access opening 20 into which a patient can insert his hand. Each tray 11 also has infill of soft resilient open cell polyurethane foam 22 which will conform to the shape of a patient's hand. Each foam infill 22 has greater depth than its moulded tray 11, thereby leaving a gap 21 between side walls of trays 11, limiting danger of damaging a patient's hand.

Figure 5:
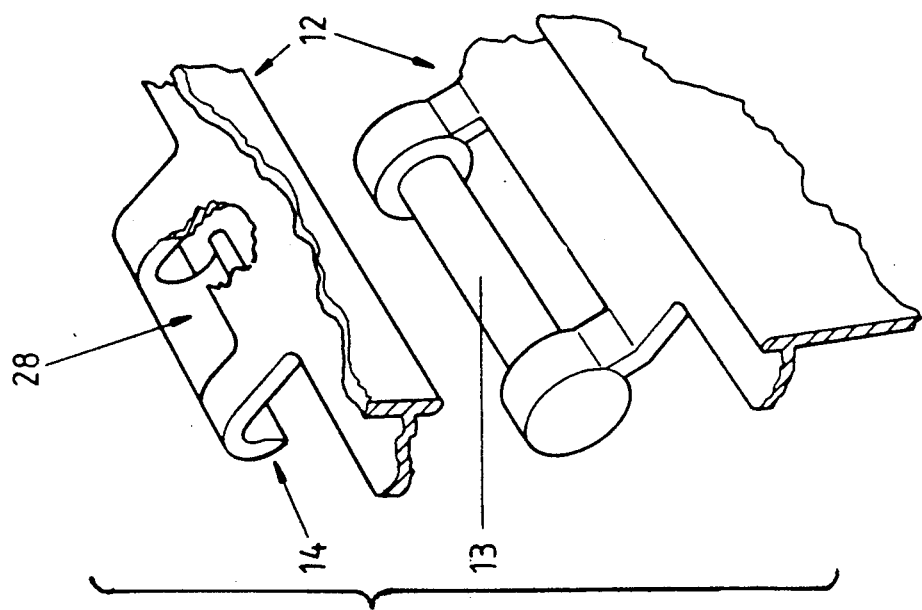
FIG. 5 is an "exploded" perspective view of the hinge which is used in this embodiment.

Two films are placed one over the foam of each tray, and the edges of the films are retained to the side edges of the applicator by means of retaining clips 23 which are best seen in FIGS. 3 and 4. Each retaining clip 23 comprises a hinge member 24 which resiliently engages an outstanding projection 25, extending part-way along and outstanding from a wall of a tray 11. The hinge members 24 hinge on hinges 26 the shapes of which are somewhat similar to the shape shown in FIG. 5. This hinge arrangement is very convenient since assembly is effected by merely pushing the hinge over the bar. It may be noted that the claw 14 extends beyond an access aperture 28 as seen in FIG. 5 to simplify the moulding of the return portion of claw 14.

In use, paper covering is removed from the films, the film edges are stretched and retained by retainer clips 23, and the adhesive surfaces are arranged to face each other. A patient's hand is inserted and the trays closed over it. The foam infill pads 22 tension the clips 16 and retain closure. The films adhere to one another around the hand and between the fingers, and surplus film is then removed from around the hand, leaving a generally air-tight "glove" on the hand.

A brief consideration of the above embodiment will indicate that the invention provides identical (or almost identical) parts so that a single moulding can be used for making both trays 11. All hinges can be produced using a similar mould with inserts. Closing the retaining clips 23 draws the film over projections 24 and has the effect of applying tension to the film to thereby stretch the film over the surface of the foam 22, reducing likelihood of wrinkles when the foam is applied to a user's hand. Wrinkles may otherwise allow entry of air. The clips 16 are retained in their engaged position by the resilience of the foam.

Quite clearly the invention may be extended, and for example many instances occur wherein a finger is damaged, and in another embodiment a much reduced size applicator utilises one hinge and one clip only, but in other respects corresponds to the applicator described above, but of course on a much reduced scale.

Figure 2:
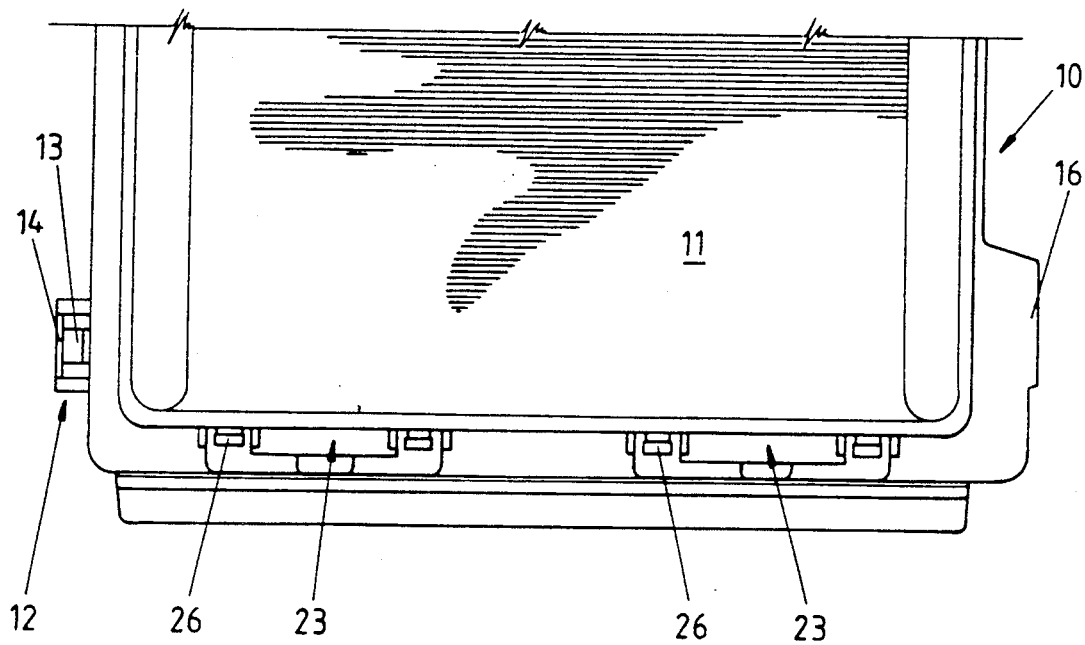
FIG. 2 is a fragmentary plan view showing the way in which a hand can be positioned in an applicator.

Sometimes a person's foot becomes damaged due to some accident, and the applicator described above can also be used for many foot wounds. In order to support the applicator at the right angle to receive a patient's foot, there is provided a base in which the applicator may nest or to which it may be temporarily secured. The applicator when so carried by the base can be at an angle compared with the horizontal position shown in FIGS. 1 and 2. However these and other similar variations will be seen to lie within the invention.

The claims defining the invention are as follows:

1. An applicator for applying adhesive plastics film to extremities of the human body, comprising:
   a pair of moulded trays, respective soft resilient foam pads in each said tray of depth greater than the depth of the tray, a hinge joining corresponding first ends of the trays such that the foam pads are openable away from each other or closable to lie in face-to-face contiguity, and when so closed, leave gaps between the sides of the trays,
   latch means releasably joining second ends of the trays which are opposite the first ends when the foam pads are in their face-to-face contiguity, each second end having a recess flange which co-operates with the recess flange of the other second end to form an access opening at the second end into which a patient can insert an extremity,
   and film retaining clips extending along opposite sides of at least one of the trays.

2. An applicator according to claim 1 wherein the trays are of generally identical shape and size.

3. An applicator according to claim 1 or claim 2 wherein each said hinge comprises a bar on one said moulded tray and a part-circular claw on the other said moulded tray which engages part way around the bar.

4. An applicator according to claim 1 wherein each said film retaining means comprises a clip which engages a projection which extends part way along a side of either of said trays, each said clip comprising a hinge member which resiliently engages a projection.

5. An applicator according to claim 4 wherein each said clip hinge member when engaging a said projection moves over the projection in a manner to tension a film retained thereby.

* * * * *